(12) United States Patent
Sugiyama et al.

(10) Patent No.: US 8,802,366 B2
(45) Date of Patent: Aug. 12, 2014

(54) MEASUREMENT METHOD USING ENZYME

(71) Applicants: ARKRAY, Inc., Kyoto (JP); Kikkoman Biochemifa Company, Chiba (JP)

(72) Inventors: Koji Sugiyama, Kyoto (JP); Satoshi Yonehara, Kyoto (JP); Kazuhiko Shimoji, Saitama (JP)

(73) Assignees: ARKRAY, Inc., Kyoto (JP); Kikkoman Biochemifa Company, Chiba (JP)

( * ) Notice: Subject to any disclaimer, the term of this patent is extended or adjusted under 35 U.S.C. 154(b) by 0 days.

(21) Appl. No.: 13/792,798

(22) Filed: Mar. 11, 2013

(65) Prior Publication Data

US 2013/0244264 A1    Sep. 19, 2013

(30) Foreign Application Priority Data

Mar. 15, 2012 (JP) ................. 2012-058516
Mar. 7, 2013 (JP) ................. 2013-045758

(51) Int. Cl.
*C12Q 1/00* (2006.01)
*C12Q 1/37* (2006.01)
*C12Q 1/26* (2006.01)

(52) U.S. Cl.
USPC ............ 435/4; 435/23; 435/24; 435/25

(58) Field of Classification Search
USPC .......................... 435/4, 23, 24, 25
See application file for complete search history.

(56) References Cited

U.S. PATENT DOCUMENTS

| | | | |
|---|---|---|---|
| 4,945,053 A | 7/1990 | Ito et al. | |
| 4,962,030 A | 10/1990 | Kawai et al. | |
| 5,449,613 A * | 9/1995 | Dordick et al. | 435/41 |
| 6,127,138 A | 10/2000 | Ishimaru et al. | |
| 6,797,503 B1 | 9/2004 | Ishimaru et al. | |
| 6,825,016 B1 | 11/2004 | Ishimaru et al. | |
| 7,070,948 B1 | 7/2006 | Sakaue et al. | |
| 2003/0162242 A1 | 8/2003 | Yonehara | |
| 2004/0248226 A1 | 12/2004 | Yonehara et al. | |
| 2006/0240501 A1 | 10/2006 | Ebinuma | |
| 2007/0037243 A1 | 2/2007 | Hirokawa et al. | |
| 2007/0154976 A1 | 7/2007 | Taniguchi et al. | |
| 2008/0233605 A1 | 9/2008 | Taniguchi et al. | |
| 2009/0239239 A1 | 9/2009 | Hirokawa et al. | |

FOREIGN PATENT DOCUMENTS

| | | |
|---|---|---|
| EP | 1693461 A1 | 8/2006 |
| JP | 8-509367 A | 10/1996 |
| JP | 10-262695 A | 10/1998 |
| JP | 2000-300294 A | 10/2000 |
| JP | 2001-057897 A | 3/2001 |
| JP | 2001-069974 A | 3/2001 |
| JP | 2001-095598 A | 4/2001 |
| JP | 2001-258593 A | 9/2001 |
| JP | 2004-333455 A | 11/2004 |
| JP | 2005-110657 A | 4/2005 |
| JP | 2005-172533 A | 6/2005 |
| JP | 2008-108385 A | 5/2008 |
| WO | 91/03550 A1 | 3/1991 |
| WO | 94/25574 A1 | 11/1994 |
| WO | 98/48043 A1 | 10/1998 |
| WO | 00/50579 A1 | 8/2000 |
| WO | 00/61732 A1 | 10/2000 |
| WO | 02/06519 A1 | 1/2002 |
| WO | 03/033729 A1 | 4/2003 |
| WO | 2004/038034 A1 | 5/2004 |
| WO | 2005/049857 A1 | 6/2005 |
| WO | 2005/049858 A1 | 6/2005 |
| WO | 2007/125779 A1 | 11/2007 |
| WO | 2008/108385 A1 | 9/2008 |

OTHER PUBLICATIONS

Hirokawa et al. An Enzymatic Method for the Determination of Hemoglobin A1C; Biotechnology Letters, vol. 27 (2005) pp. 963-968.*
Extended European Search Report issued in corresponding European Patent Application No. 13159623.1 dated Jun. 5, 2013.
Hirokawa et al., "Enzymes used for the determination of HbA1C," FEMS Microbiology Letters, 235: 157-162 (2004).
"Savinase CLEA," CLEA Technologies, Copyright 2011.
"Savinase: A hard-working, robust protease used to remove protein-based stains," Novozymes (2010).
"Savinase CLEA," CLEA Technologies.
Chen et al., "A New Enzymatic Kit for Measuring Glycated Serum Protein with DA-64 as a Chromogen," Jiangxi Journal of Medical Laboratory Sciences, 25: 295-298 (2007) (see partial translation).
Office Action issued in counterpart Chinese Patent Application No. 201310084573.2 dated Apr. 10, 2014 (see partial translation).

* cited by examiner

*Primary Examiner* — Susan Hanley
*Assistant Examiner* — Paul Martin
(74) *Attorney, Agent, or Firm* — Morgan, Lewis & Bockius LLP

(57) ABSTRACT

A method for measuring an analyte is described that includes the steps of: i) preparing a reagent (D) in which an enzyme (A) and an enzyme (B) coexist in the absence of the analyte; ii) bringing the analyte into contact with the enzyme (A) and the enzyme (B) so that the enzyme (A) acts on the analyte to produce a product (E), on which the enzyme (B) does not substantially act, from the analyte; iii) producing a product (C) by allowing the enzyme (A) or an enzyme (F) that is different from the enzyme (A) that acts on the analyte to produce a product (C) to act on the analyte and/or the product (E); and iv) detecting the product (C) by the enzyme (B).

9 Claims, 2 Drawing Sheets

MEASUREMENT METHOD USING ENZYME

BACKGROUND OF THE INVENTION

1. Field of the Invention

The present invention relates to a measurement method using an enzyme, and a reagent kit used for the measurement method.

2. Description of Related Art

There are many methods for measuring an analyte using an enzyme, and the methods are broadly divided into two types. In the first type, an enzyme having specificity for an analyte acts directly on the analyte, thereby detecting the analyte. Examples of the first type include the following: a method in which the analyte is glucose and the enzyme is glucose oxidase or glucose dehydrogenase; and a method in which the analyte is uric acid and the enzyme is uricase. In the second type, an enzyme acting on an analyte is used to produce a product derived from the analyte, and then an enzyme having specificity for the product acts on the product, thereby detecting the analyte. Examples of the second type include the following: a method in which the analyte is a glycated protein, the enzyme acting on the analyte is a protease, and the enzyme having specificity is a fructosyl amino acid oxidase (FAOD); a method in which the analyte is cholesterol, the enzyme acting on the analyte is cholesterol esterase, and the enzyme having specificity is cholesterol oxidase; and a method in which the analyte is creatinine, the enzyme acting on the analyte is creatininase, and the enzyme having specificity is sarcosine oxidase.

In the second type of method, the enzyme having specificity for the product and the enzyme acting on the analyte may be added in the following order: 1) the enzyme having specificity for the product is added after the enzyme acting on the analyte; 2) the enzyme having specificity for the product is added prior to the enzyme acting on the analyte; or 3) the enzyme acting on the analyte and the enzyme having specificity for the product are added simultaneously.

When the enzyme having specificity for the product is added after the enzyme acting on the analyte, since a product with which the enzyme having the specificity is to react has been produced in advance from the analyte, this method has the advantage of allowing the enzyme having specificity to react with the product quickly.

When the enzyme having specificity for a product is added prior to the enzyme acting on the analyte, this method has the advantage of removing a substance that impairs the measurement accuracy. If the product derived from the analyte that is to be produced by the enzyme acting on the analyte is already present as an endogenous substance in a sample, the endogenous substance can impair the measurement accuracy. The addition of the enzyme having specificity for a product prior to the enzyme acting on the analyte can remove the endogenous substance beforehand.

When the enzyme acting on the analyte and the enzyme having specificity for a product are added simultaneously, this method has the advantage of providing those enzymes as a single reagent.

A method for measuring a glycated protein using an enzyme has been known, in which a protease acts on the glycated protein to produce a glycated amino acid or a glycated peptide, and then a FAOD acts on the glycated amino acid or the glycated peptide, so that hydrogen peroxide is generated and measured.

Although several types of FAODs are used in accordance with their substrate specificities, all of them react only with a glycated amino acid or a short glycated peptide. For example, WO 2008-108385 and WO 2004-038034 disclose the FAOD that reacts with a glycated peptide comprising 6 amino acids. However, the FAOD that reacts with a glycated peptide having more than 6 amino acids and the FAOD that reacts directly with the glycated protein have not been known.

Therefore, in order to measure the glycated protein with the FAOD, the glycated protein needs be decomposed into a glycated amino acid or a glycated peptide having not more than 6 amino acids. The decomposition method includes, e.g., a chemical process using an acid or alkali. In view of the labor savings and convenience, the most effective decomposition method is to combine a protease and a glycated protein denaturing agent. In this method, e.g., a measurable degree of the glycated amino acid or the glycated peptide can be produced from the glycated protein in about 5 minutes.

The glycated protein is generated when a sugar such as glucose is bound to the N-terminal amino group or the side-chain amino groups of lysine and arginine in the middle of the protein. Therefore, the glycation occurs in a plurality of sites of the protein molecules. Accordingly, there are a great many types of glycated proteins in which any one or more than one of the N-terminal amino groups and/or the amino groups of lysine and arginine in the middle of the protein are glycated.

In the case of HbA1c in which only the N-terminus of the β-chain of hemoglobin is glycated, a method for specifically measuring only the glycated site (i.e., the glycated site at the N-terminus of the (β-chain) has been put to practical use. On the other hand, a method for measuring some of the glycated sites of the glycated protein has been generally employed. This is because measuring only one particular glycated site of lysine and arginine in the middle of the protein is not practical, since the protease should act specifically on the particular glycated site so that a glycated amino acid or a glycated peptide is produced only from that particular glycated site, and the rate of glycation of the individual sites may vary depending on the state of the protein.

It is known that a glycated amino acid is easily produced when a sugar such as glucose coexists with an amino acid. In order to increase the time during which the protease is acting on the glycated protein, the protease is preferably added first. On the other hand, however, a sample may contain a glycated amino acid. Therefore, it is desirable that such a glycated amino acid is eliminated from the sample by adding the FAOD prior to the protease so as to measure the amount of the glycated protein accurately. If one type of protease is added after the FAOD and is used to produce a glycated amino acid or a glycated peptide derived from all the glycated sites of the glycated protein, it is necessary that either the concentration of the protease is increased, a protease with a low specificity is used, or the protease acts for a long time.

Thus, the use of a plurality of types of proteases also has been considered. In the measurement of HbA1c, it is difficult for a protease to act directly on the N-terminus of the β-chain of hemoglobin. Therefore, a method using two types of proteases has been proposed. Examples of this method include the following: a method that uses an enzyme for liberating an amino acid having a glycated α-amino group and another protease (WO 2000-50579 and WO 2000-061732); a method that includes an enzymatic treatment with a serine carboxypeptidase and a suitable endoprotease or exoprotease (JP 2001-57897 A); a method that includes a treatment with a protease capable of cleaving the carboxyl group side of the third leucine from the N-terminus of the β-chain of hemoglobin, and subsequently a treatment with a protease capable of cutting histidyl leucine from the generated fructosyl valyl histidyl leucine (JP 2000-300294 A); and a method that combines Glu-C and another protease (JP 2005-110657 A).

In the measurement of glycated albumin or glycated hemoglobin using a plurality of types of proteases, e.g., the following methods have been disclosed: a method that causes a protease reaction and allows the other endoprotease or exoprotease to act before and after the protease reaction or at the same time as the protease reaction (JP 2004-333455 A); a method that uses an endoprotease, an exoprotease, etc. either individually or in combination (JP 1998-262695 A, JP 2005-172533 A, JP 2001-095598 A, WO 2005-049858, WO 2005-049857, and JP 2001-258593 A); and a method that uses a selectively decomposable protease and a general protease (WO 2002-006519).

It is easily expected that the protease also decomposes and inactivates the FAOD, which is a protein. The following methods have been disclosed to address the problem of the inactivation of the FAOD by the protease. WO 1998-048043 discloses a method that inactivates a protease before a FAOD treatment to prevent the inactivation of the FAOD by the protease. WO 2007-125779 discloses a method that uses a FAOD that is highly resistant to a protease. WO 2003-033729 discloses a method that makes good use of the inactivation of a FAOD by a protease.

SUMMARY OF THE INVENTION

The disadvantage of the addition of the enzyme having specificity prior to the enzyme acting on the analyte is that if the action of the enzyme on the analyte is not immediately completed, the concentration of the substrate for the enzyme having specificity is reduced, resulting in low reactivity. In particular, it can be a great disadvantage if the product that has been produced by the enzyme acting on the analyte reacts again with the enzyme to produce a substance, and the enzyme having specificity is capable of acting on this substance.

Such a disadvantage poses a significant problem, particularly in measuring the glycated protein. When all or a plurality of the glycated sites of the glycated protein are to be measured, the whole of the glycated protein or a large glycated peptide fragment needs to be decomposed into a glycated amino acid or a short glycated peptide using one type of protease. Therefore, a protease with a relatively low specificity is required. Moreover, a very large amount of protease has to be added to produce a glycated amino acid or a short glycated peptide in a short time. However, it is known that even if a large amount of protease is added, the glycated amino acid or the short glycated peptide cannot be produced in a short time, since the rate of action of the protease is limited. When the protease is added in a large amount, it also acts on and may inactivate the coexisting enzyme proteins such as FAOD and POD. Accordingly, a large amount of enzymes such as FAOD and POD should be added. Because of the fact that the protease itself is a protein, the addition of a large amount of protease may reduce the stability of the protease due to autolysis and inhibit the protease reaction, so that the glycated protein cannot be decomposed in a short time. Moreover, when the protease is used at a high concentration or allowed to act for a long time, there is also a possibility that the protease will act on a glycated protein other than the target protein, or autolysis of the protease occurs.

On the other hand, the combination of two types of proteases has the following problems. WO 2000-50579 and WO 2000-061732 disclose a method that uses a protease (second protease) for liberating an amino acid having a glycated α-amino group and another protease (first protease). The second protease has a narrow substrate specificity, as represented by the protease for liberating an amino acid having a glycated α-amino group. The first protease is not particularly disclosed or limited, but is merely described in such a way that "the glycated protein or the like may be decomposed by another enzyme (e.g., protease)".

JP 2001-57897 A discloses a method that includes an enzymatic treatment with a serine carboxypeptidase (second protease) and a suitable endoprotease or exoprotease (first protease). The second protease has a limited substrate specificity, as represented by the serine carboxypeptidase. In JP 2001-57897 A, the first protease is not particularly disclosed or limited, but is merely described in such a way that "the above-described N-terminal-valine fructosylated peptide may be prepared by treating a peptide or protein having such a sequence with, e.g., a suitable endoprotease or exoprotease. Examples of the protease include elastase, proteinase K, pepsin, alkaline protease, trypsin, proline-specific endoprotease, V8 protease, carboxypeptidase A, and carboxypeptidase B".

JP 2000-300294 A discloses a method that includes a treatment with a protease capable of cleaving the carboxyl group side of the third leucine from the N-terminus of the β-chain of hemoglobin, and a treatment with a protease capable of cutting histidyl leucine from the generated fructosyl valyl histidyl leucine. In JP 2000-300294 A, the protease (capable of cleaving the carboxyl group side of the third leucine from the N-terminus of the β-chain of hemoglobin) has a very high specificity and does not act on HbA1c (glycated protein), and thus is identified as the second protease. Therefore, the first protease that can decompose HbA1c in advance is essential, but is not particularly disclosed or limited.

JP 2005-110657 A describes that HbA1c is treated with an endoproteinase Glu-C to produce an α-glycated hexapeptide, and then a protease capable of liberating an α-glycated dipeptide acts on the α-glycated hexapeptide. However, there is no particular disclosure or limitation.

JP 1998-262695 A, JP 2005-172533 A, JP 2001-095598 A, WO 2005-049858, WO 2005-049857, JP 2001-258593 A, and WO 2002-006519 disclose that the rate of decomposition of the glycated protein is improved by combining a plurality of types of proteases. However, none of them discloses the possibility that the FAOD may be decomposed by the protease if the FAOD coexists with the protease, and the use of the FAOD and the protease together in the same reagent.

WO 1998-048043 discloses that the number of steps is increased to three (protease treatment, protease inactivation treatment, and FAOD treatment) to inactivate the protease before the FAOD treatment. However, the number of steps should be few in general. Moreover, this document does not disclose that the FAOD coexists with the protease.

WO 2007-125779 discloses that the protease inactivates the FAOD for a short time during the measurement of the glycated protein, but does not disclose or suggest the use of the FAOD and the protease together in the same reagent. Moreover, this document fails to disclose that FAODs have various substrate specificities and may differ in resistance to the protease. Further, it is difficult to find the protease resistance of all of the FAODs.

The following three types of configurations of reagents for measuring the glycated protein have been disclosed:

Conventional Example 1: first reagent=protease, second reagent=FAOD

Conventional Example 2 first reagent=FAOD, second reagent=protease

Conventional Example 3: first reagent=FAOD, second reagent=protease, third reagent=FAOD With the foregoing in mind, the present disclosure provides a method for measuring an analyte using an enzyme (A) (e.g., protease) that acts on the analyte (e.g., glycated protein) to produce a product (C), and an enzyme (B) (e.g., FAOD) that specifically detects the product (C), in which the product (C) can be produced from the analyte more easily and efficiently.

The present disclosure is directed to a method for measuring an analyte using an enzyme (A) that acts on the analyte and an enzyme (B) that specifically detects a product (C) produced from the analyte. The method includes the following: i) preparing a reagent (D) in which the enzyme (A) and the enzyme (B) coexist in the absence of the analyte; ii) bringing the analyte into contact with the reagent (D) so that the enzyme (A) acts on the analyte to produce a product (E), on which the enzyme (B) does not substantially act, from the analyte; iii) producing a product (C) by allowing the enzyme (A) or an enzyme (F) that is different from the enzyme (A) to act on the analyte and/or the product (E); and iv) detecting the product (C) by the enzyme (B). Hereinafter, the method is also referred to as a "measurement method of the present disclosure".

The measurement method of the present disclosure results in producing the product (C) from the analyte efficiently in a shorter time, and improving the measurement accuracy of the analyte.

DETAILED DESCRIPTION OF THE INVENTION

Figure 1:
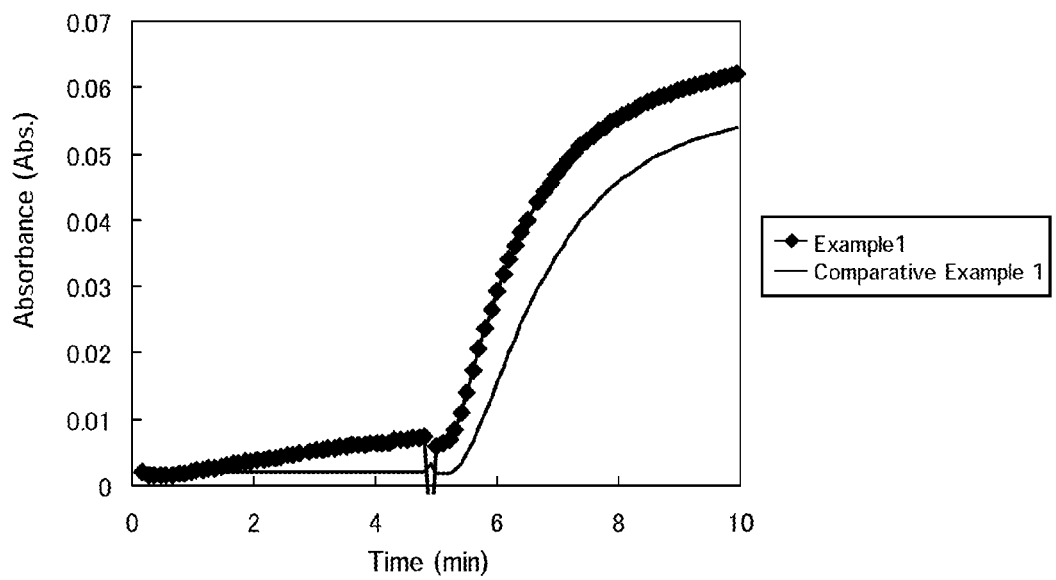
FIG. 1 is a graph showing the results of Example 1 and Comparative Example 1.

The present disclosure is based on the findings that in a method for measuring an analyte using an enzyme (A) that acts on the analyte to produce a product (C) and an enzyme (B) that specifically detects the product (C), the product (C) can be produced efficiently in a shorter time with the use of a reagent in which the enzyme (A) and the enzyme (B) coexist. Moreover, the present disclosure is based on the findings that in a method for measuring an analyte using an enzyme (A) that acts on the analyte to produce a product (C) and an enzyme (B) that specifically detects the product (C), the product (C) can be produced efficiently in a shorter time by bringing the analyte into contact with the enzyme (A) and the enzyme (B) that coexist.

In the measurement method of the present disclosure, the use of the reagent in which the enzyme (A) and the enzyme (B) coexist has the following advantages. First, the enzyme (A) changes the analyte to a form from which the product (C) can be produced more easily, so that the rate of formation of the product (C) can be improved. Second, the enzyme (B) can remove endogenous substances that may cause a measurement error. More specifically, in the measurement method of the present disclosure, the analyte is brought into contact with the reagent (D) in which the enzyme (A) and the enzyme (B) coexist, that is, the analyte is brought into contact with the enzyme (A) and the enzyme (B) that coexist in the reagent (D). Thus, in one or more embodiments, the rate of formation of the product (C) can be improved by the enzyme (A) while endogenous substances that may cause a measurement error can be removed by the enzyme (B).

Analyte

In the present specification, the analyte may be, e.g., a glycated protein, a protein, urea, a fatty acid such as triglyceride, creatinine, glucose, or the like that can be measured by the measurement method of the present disclosure. Examples of the glycated protein include glycated hemoglobin, glycated albumin, HbA1c, and a combination thereof.

Enzyme (A) that Acts on Analyte to Produce Product (C) and Enzyme (F)

In the present specification, the phrase "the enzyme (A) that acts on the analyte to produce the product (C) or the enzyme (A) that acts on the analyte" means an enzyme that acts on the analyte to produce (or to be able to produce) the product (C) or an enzyme that acts on the analyte to produce (or to be able to produce) the product (E) from which the product (C) can be produced. In one or more embodiments, the enzyme (A) of the present disclosure may be, e.g., a protease, a lipoprotein lipase, creatininase, a hexokinase, amylase, or the like.

In one or more embodiments of the present specification, the enzyme (F) is different from the enzyme (A) and may be, e.g., an enzyme that is categorized as the same protease, a kinase that produces the product (C), creatinase, glucose-6-phosphate dehydrogenase, an α-glucosidase, or the like. In one or more embodiments, examples of the kinase that produces the product (C) include pyruvate kinase and glycerol kinase.

Enzyme (B) that Specifically Detects Product (C)

In one or more embodiments of the present specification, the "enzyme (B) that specifically detects the product (C)" may be, e.g., fructosyl amino acid oxidase (FAOD), an amino acid oxidase, pyruvate oxidase, glycerol-3-phosphate oxidase, sarcosine oxidase, diaphorase, or the like. In one or more embodiments, examples of the amino acid oxidase include an amino acid oxidase that acts specifically on tryptophan (JP 2001-69974A) and an amino acid oxidase that acts specifically on lysine (JP 8 (1996)-509367 A).

Product (C)

In the present specification, the "product (C)" is produced directly from the analyte or is produced from the product (E) that has been produced from the analyte. The "product (C)" is produced by the action of the enzyme (F) or the enzyme (A) on the analyte and/or the product (E). In one or more embodiments, the "product (C)" of the present disclosure may be, e.g., a glycated amino acid, a glycated peptide that includes a glycated amino acid and has 2 to 6 amino acid residues, pyruvic acid, glycerol-3-phosphate, sarcosine, NADH, or the like.

Product (E)

In the present specification, the "product (E) on which the enzyme (B) does not substantially act" is produced by the action of the enzyme (A) on the analyte, and can produce the product (C) by the action with the enzyme (A) or the enzyme (F). In one or more embodiments, the "product (E)" of the present disclosure may be, e.g., a glycated peptide having 2 to 6 or more amino acid residues, glucose-6-phosphate, ADP, glycerol, creatine, cholesterol, or the like.

The following table shows one or more embodiments of combinations of the analyte, the enzyme (A), the product (E), the enzyme (F), the product (C), and the enzyme (B).

TABLE 1

| Analyte | Enzyme (A) | Product (E) | Enzyme (F) | Product (C) | Enzyme (B) |
|---|---|---|---|---|---|
| glycated protein | protease | glycated peptide | protease different from enzyme (A) | glycated amino acid/ glycated peptide | FAOD |
| glucose | hexokinase | glucose-6-phosphate | pyruvate kinase | pyruvic acid | pyruvate oxidase |
| fatty acid | lipoprotein lipase | glycerol | glycerol kinase | glycerol-3-phosphate | glycerol-3-phosphate oxidase |
| creatinine | creatininase | creatine | creatinase | sarcosine | sarcosine oxidase |
| creatinine | creatininase | creatine | creatinase | sarcosine | sarcosine dehydrogenase |
| starch | amylase | maltose | α-glucosidase | glucose | glucose oxidase |
| protein | protease | peptide | peptidase | amino acid | amino acid oxidase |
| total cholesterol | cholesterol esterase | cholesterol | cholesterol dehydrogenase | NADH | diaphorase |

In one or more embodiments, examples of the protease include thermolysin, trypsin, α-chymotrypsin, Alcalase, a neutral protease, and an alkaline protease. In one or more embodiments, examples of the trypsin include trypsin from porcine pancreas and trypsin from bovine pancreas. In one or more embodiments, examples of the α-chymotrypsin include α-chymotrypsin from bovine pancreas. In one or more embodiments, examples of the alkaline protease include Alcalase™ (manufactured by Novozymes, *Bacillus licheniformis*) and subtilisin 309 (product name: Savinase® manufactured by Novozymes, *Bacillus* sp.).

When the enzyme (A) is a protease, the combination of the enzyme (A) and the enzyme (F) is not particularly limited. In one or more embodiments, examples of the combination include the following: 1) the enzyme (A) is a protease and the enzyme (F) is a protease that is different from the enzyme (A); and 2) the enzyme (A) is selected from thermolysin, trypsin, α-chymotrypsin, Alcalase, a neutral protease, and an alkaline protease and the enzyme (F) is an alkaline protease (except for the alkaline protease used as the enzyme (A)). In one or more embodiments, the "protease that is different from the enzyme (A)" of the present disclosure may be, e.g., a protease that differs from the enzyme (A) in at least any one of the following: substrate, substrate specificity, cleavage site, active structure, and optimum pH.

Reagent (D)

One of the technical characteristics of the measurement method of the present disclosure is to use the reagent (D) in which the enzyme (A) and the enzyme (B) coexist. In an embodiment, the reagent (D) is a commercially available package that includes the enzyme (A), the enzyme (B), and a container in which these enzymes are packaged, or a reagent in part of the commercially available package.

When the enzyme (A) is a protease, it is difficult for the protease to coexist with other enzymes because the protease is an enzyme that decomposes proteins. For this reason, the protease and other enzymes (e.g., FAOD) have not been used together in the same reagent.

Measurement Method

The measurement method of the present disclosure is a method for measuring an analyte that includes at least four steps of: i) preparing a reagent (D) in which the enzyme (A) and the enzyme (B) coexist in the absence of the analyte; ii) bringing the analyte into contact with the enzyme (A) and the enzyme (B) so that the enzyme (A) acts on the analyte to produce a product (E), on which the enzyme (B) does not substantially act, from the analyte; iii) producing a product (C) by allowing the enzyme (A) or an enzyme (F) that is different from the enzyme (A) that acts on the analyte to produce a product (C) to act on the analyte and/or the product (E); and iv) detecting the product (C) by the enzyme (B).

In the measurement method of the present disclosure, the contact between the analyte and the enzyme (A) and the enzyme (B) may occur by bringing the analyte into contact with the reagent (D) that has been prepared in the step i). In other words, the enzyme (A) and the enzyme (B) that are to be in contact with the analyte may be the enzyme (A) and the enzyme (B) contained in the reagent (D) that has been prepared in the step i). Moreover, the enzyme (B) that is used to detect the product (C) in the step iv) is preferably the enzyme (B) that has been in contact with the analyte in the step ii).

In one or more embodiments, the reagent (D) in which the enzyme (A) and the enzyme (B) coexist in the step i) may be prepared by mixing the enzyme (A) and the enzyme (B) immediately before the contact with the analyte in the step ii), or the reagent (D) may be previously prepared and stored. However, in terms of suppressing a reduction in activity of the enzyme (A) and/or the enzyme (B) due to the long-term storage of the reagent (D), it is preferable that the reagent (D) is prepared by mixing the enzyme (A) and the enzyme (B) immediately before the contact with the analyte.

The measurement method of the present disclosure has at least three embodiments for the step iii).

In the first embodiment, the enzyme (A) is added twice, which means that the step iii) is performed by further adding the enzyme (A) after the step ii).

In the second embodiment, the enzyme (A) and the enzyme (F) are added separately, which means that the step iii) is performed by adding the enzyme (F) after the step ii).

In the third embodiment, the enzyme (A) is added once, and then activated, which means that the step iii) is performed by activating the enzyme (A) after the step ii). In the third embodiment, the enzyme (A) that acts on the analyte and/or the product (E) in the step iii) may be the enzyme (A) contained in the reagent (D) that has been prepared in the step i).

In the measurement method of the present disclosure, in one or more embodiments, the detection in the step iv) may be performed by absorbance determination or electrochemical determination.

In the measurement method of the present disclosure, in one or more embodiments, the enzyme (A), the enzyme (B), the reagent (D) containing the enzyme (A) and the enzyme (B), and the enzyme (F) may be in the form of a liquid reagent, a dry reagent obtained by freeze drying or hot-air drying, or the like. When the dry reagent is used, it may be dissolved before the measurement, or may be mixed with and dissolved in a liquid sample.

Another aspect of the present disclosure is directed to a method for measuring an analyte using an enzyme (A) that acts on the analyte to produce a product (C) and an enzyme (B) that specifically detects the product (C). The method includes the following: ii') bringing the analyte into contact with a dry reagent (D) containing the enzyme (A) and the enzyme (B) so that the enzyme (A) acts on the analyte to produce a product (E), on which the enzyme (B) does not substantially act, from the analyte; iii') producing a product (C) by allowing the enzyme (A) to act on the analyte and/or the product (E); and iv) detecting the product (C) by the enzyme (B). In the measurement method of this aspect, the enzyme (A), the enzyme (B), the product (C), and the product (E) have been described above.

In one or more embodiments, the dry reagent (D) includes a first reagent layer that includes a reagent layer containing the enzyme (A) and a reagent layer containing the enzyme (B). In one or more embodiments, the dry reagent (D) may be either in the state in which the enzyme (A) and the enzyme (B) are mixed or in the state in which the layer containing the enzyme (A) and the layer containing the enzyme (B) are laminated.

In one or more embodiments, the dry reagent (D) may contain the enzyme (F). The enzyme (F) can be the same as that described above. In one or more embodiments, the dry reagent (D) includes a second reagent layer in addition to the first reagent layer, and the second reagent layer contains the enzyme (F). In one or more embodiments, the dry reagent (D) may have any of the following configurations: 1) the layer containing the enzyme (A), the layer containing the enzyme (B), and the layer containing the enzyme (F) are laminated or arranged in parallel on a base member; 2) the layer containing the enzyme (B), the layer containing the enzyme (A), and the layer containing the enzyme (F) are laminated or arranged in parallel on a base member; and 3) the layer containing the enzyme (A) and the enzyme (B) and the layer containing the enzyme (F) are laminated or arranged in parallel on a base member. In each of the above configurations, the layers are disposed in the indicated order from the side that comes into contact with the analyte.

In one or more embodiments, the step iii') may include producing a product (C) by allowing the enzyme (A) and the enzyme (F) to act on the analyte and/or the product (E).

Hereinafter, one or more embodiments of the measurement method of the present disclosure will be described without any particular limitation, where the analyte is a glycated protein, the enzyme (A) and the enzyme (F) are proteases, and the enzyme (B) is a FAOD.

First Embodiment

The first embodiment includes the following: i) preparing a first reagent in which a protease and a FAOD coexist in the absence of a glycated protein; ii) bringing the glycated protein into contact with the protease and the FAOD so that the protease acts on the glycated protein to produce a product, on which the FAOD does not substantially act, from the analyte; iii) producing a substrate (a glycated amino acid and/or a glycated peptide) for the FAOD by allowing a second reagent containing the same protease as that of the first reagent to act on the glycated protein and/or the product; and iv) detecting the substrate by the FAOD.

It is preferable that the reaction conditions of the step ii) in the first embodiment are defined so that a glycated amino acid or a short glycated peptide that can react with the FAOD is not substantially produced from the glycated protein (analyte).

The first embodiment can be performed using a reagent kit that includes the first reagent containing the FAOD and the protease and the second reagent containing the same protease as that of the first reagent.

As an example of the method in the first embodiment of the present disclosure, the sample is brought into contact with the first reagent containing the FAOD and the protease, and then the second reagent containing the same protease as that of the first reagent is added. Thus, according to the method in the first embodiment of the present disclosure, in one or more embodiments, the analyte can be measured using only two types of reagents of the first reagent containing the FAOD and the protease and the second reagent containing the same protease as that of the first reagent.

Under the storage conditions of the first reagent, it is preferable that the activity of the FAOD is not substantially reduced by the protease, and both the protease and the FAOD can be stably present. Moreover, under the storage conditions of the first reagent, it is preferable that the protease is maintained in an active state, or that the protease is maintained in an inactive state in the first reagent and will be activated as it is mixed with the sample. When the protease has a broad substrate specificity, the protease is preferably used at a low concentration in the first reagent.

Second Embodiment

The second embodiment includes the following: i) preparing a first reagent in which a protease and a FAOD coexist in the absence of a glycated protein; ii) bringing the glycated protein into contact with the protease and the FAOD so that the protease acts on the glycated protein to produce a product, on which the FAOD does not substantially act, from the analyte; iii) producing a substrate (a glycated amino acid and/or a glycated peptide) for the FAOD by allowing a second reagent containing a different protease from that of the first reagent to act on the glycated protein and/or the product; and iv) detecting the substrate by the FAOD.

It is preferable that the reaction conditions of the step ii) in the second embodiment are defined so that a glycated amino acid or a short glycated peptide that can react with the FAOD is not substantially produced from the glycated protein (analyte).

The second embodiment can be performed using a reagent kit that includes the first reagent containing the FAOD and the protease and the second reagent containing a different protease from that of the first reagent.

As an example of the method in the second embodiment of the present disclosure, the sample is brought into contact with the first reagent containing the FAOD and the protease, and then the second reagent containing a different protease from that of the first reagent is added. Thus, according to the method in the second embodiment of the present disclosure, in one or more embodiments, the analyte can be measured using only two types of reagents of the first reagent containing the FAOD and the protease and the second reagent containing a different protease from that of the first reagent.

Under the storage conditions of the first reagent, it is preferable that the activity of the FAOD is not substantially reduced by the protease, and both the protease and the FAOD can be stably present. Moreover, under the storage conditions of the first reagent, it is preferable that the protease is maintained in an active state, or that the protease is maintained in an inactive state in the first reagent and will be activated as it is mixed with the sample. When the protease has a broad substrate specificity, the protease is preferably used at a low concentration in the first reagent. However, a protease with a narrow substrate specificity is suitable for the first reagent. Examples of the protease with a narrow substrate specificity include trypsin, Glu-C, Lys-C, and Asp-N.

A preferred protease for the second reagent in the second embodiment acts on a large peptide derived from the glycated protein that has been produced by the protease of the first reagent, and can produce a glycated amino acid or a short glycated peptide that can react with the FAOD. Moreover, the protease of the second reagent alone may produce a glycated amino acid or a short glycated peptide that can react with the FAOD from the glycated protein if the protease of the second reagent reacts sufficiently with the glycated protein. Alternatively, even if the protease of the second reagent reacts sufficiently with the glycated protein, the protease of the second reagent alone may not produce a glycated amino acid or a short glycated peptide that can react with the FAOD from the glycated protein. When the analyte is glycated hemoglobin or glycated albumin, the protease of the second reagent is preferably a protease with a relatively broad substrate specificity.

Third Embodiment

The third embodiment includes the following: i) preparing a first reagent in which a protease and a FAOD coexist in the absence of a glycated protein; ii) bringing the glycated protein into contact with the protease and the FAOD so that the protease acts on the glycated protein to produce a product, on which the FAOD does not substantially act, from the analyte; iii) producing a substrate (a glycated amino acid and/or a glycated peptide) for the FAOD by activating the protease of the first reagent so as to act on the glycated protein and/or the product; and iv) detecting the substrate by the FAOD.

The third embodiment can be performed using a reagent kit that includes the first reagent containing the FAOD and the protease and the second reagent containing an activator for the protease of the first reagent.

As an example of the method in the third embodiment of the present disclosure, the sample is brought into contact with the first reagent containing the FAOD and the protease, and then the second reagent containing a protease activator for activating the protease of the first reagent is added. Thus, according to the method in the third embodiment of the present disclosure, in one or more embodiments, the analyte can be measured using only two types of reagents of the first reagent containing the FAOD and the protease and the second reagent containing the protease activator.

It is preferable that the reaction conditions of the step ii) in the third embodiment are defined so that the protease is either inactive or active to the extent that a glycated amino acid or a short glycated peptide that can react with the FAOD is not substantially produced from the glycated protein (analyte).

A preferred protease for the first reagent in the third embodiment can decompose the glycated protein into a glycated amino acid or a glycated peptide that can react with the FAOD when it is in an active state, but will not be completely activated when it is mixed with the sample. Under the storage conditions of the first reagent, it is preferable that the activity of the FAOD is not substantially reduced by the protease, and both the protease and the FAOD can be stably present. Moreover, under the storage conditions of the first reagent, it is preferable that the protease can be stable even in its inactive state, that the protease is maintained in a low active state, or that the protease is maintained in an inactive state in the first reagent and will be changed to a low active state as it is mixed with the sample.

The protease activator of the second reagent in the third embodiment is preferably either a substance that activates the activity of the protease or a substance that denatures the analyte so that the protease can act on the analyte. In one or more embodiments, when the protease is trypsin, the protease activator may be calcium.

In the first to third embodiments, the detection in the step iv) may include any of the following methods: 1) the hydrogen peroxide generated by the FAOD is measured by using a POD and a color-developing agent to produce a pigment, and determining the absorbance; 2) the hydrogen peroxide generated by the FAOD is measured by using a hydrogen peroxide electrode; and 3) the hydrogen peroxide generated by the FAOD is electrochemically measured in the presence of a mediator that reacts with the FAOD.

In the first to third embodiments, to accelerate the decomposition of the glycated protein by the protease, in one or more embodiments, the first reagent and/or the second reagent may include a glycated protein denaturing agent. In one or more embodiments, examples of the denaturing agent include a surface-active agent, an oxidizing agent, and a reducing agent.

Hereinafter, one or more embodiments of the present disclosure will be described without any particular limitation, where the reagent is a dry reagent, the analyte is a glycated protein, the enzyme (A) and the enzyme (F) are proteases, and the enzyme (B) is a FAOD.

This embodiment can further suppress the inactivation of the FAOD by the protease, and thus can store the FAOD more stably. When the dry reagent is used, a substrate inhibition of the protease may occur due to a high concentration of the protein in the sample. Moreover, if the amount of protease is increased to improve the reactivity, the protease itself inhibits the reaction, which in turn inhibits the decomposition reaction of the glycated protein by the protease. Therefore, the measured value can decrease. In such a case, the use of two types of proteases has the merit of being able to reduce the amount of protease and finish the reaction in a short time by recuing the protein concentration in the reaction liquid. The shortening of the reaction time is particularly effective for POCT. When the time from the collection of blood to the output of the results is shortened, it is possible to reduce the burden on patients.

The structure of the dry reagent is not particularly limited, as long as the enzymes are dissolved in sequence in the sample so as to suppress the inactivation of the FAOD or the like by the protease. There is no particular limitation to the order in which the enzymes are dissolved. In one or more embodiments, the following three orders are used.

Order 1: enzyme (A)→enzyme (B)→enzyme (F)
Order 2: enzyme (B)→enzyme (A)→enzyme (F)
Order 3: enzyme (A) and enzyme (B)→enzyme (F)

In one or more embodiments, the dry reagent may have a structure in which the reagent layers containing each of the enzymes are laminated or arranged in parallel on a base member so that the enzymes are dissolved in any of the above orders. For the orders 1 and 2, in one or more embodiments, it is preferable that the reagent layers are disposed so that the enzyme (A) and the enzyme (B) are quickly dissolved without a time difference.

Kit and Commercially Available Package

Another aspect of the present disclosure is directed to a commercially available package used for the measurement method of the present disclosure. The commercially available package includes the enzyme (A), the enzyme (B), and a container in which these enzymes are packaged. In the present specification, the reagent of the commercially available package is a commercially available reagent that is prepared by the manufacturer for the use in the measurement method of the present disclosure, rather than a reagent that is prepared in a laboratory where the measurement method of the present disclosure is performed. The enzyme (A) and the enzyme (B) may be packaged either in the same container or in different containers. As a specific example, the commercially available package of the present disclosure may include a protease, a FAOD, and a container in which the protease and the FAOD are packaged. The commercially available package of the present disclosure may be accompanied by an instruction manual for the measurement method of the present disclosure.

Yet another aspect of the present disclosure is directed to a reagent kit used for the measurement method of the present disclosure. The reagent kit includes a reagent container in which the enzyme (A) and the enzyme (B) coexist. In the present specification, the reagent kit is a commercially available reagent or combination of reagents that is prepared by the manufacturer for the use in the measurement method of the present disclosure, rather than a reagent that is prepared in a laboratory where the measurement method of the present disclosure is performed. The reagent kit of the present disclosure may further include the enzyme (A) or the enzyme (F) that is packaged in a different container, and also may be accompanied by an instruction manual for the measurement method of the present disclosure. As a specific example, the reagent kit of the present disclosure may include a reagent container in which a protease and a FAOD coexist.

Still another aspect of the present disclosure is directed to a reagent kit used for the measurement method of the present disclosure. The reagent kit includes a dry reagent (D) containing the enzyme (A) and the enzyme (B). In one or more embodiments, the dry reagent (D) may be either in the state in which the enzyme (A) and the enzyme (B) are mixed or in the state in which the layer containing the enzyme (A) and the layer containing the enzyme (B) are laminated. In one or more embodiments, the dry reagent (D) may contain the enzyme (F). In one or more embodiments, the dry reagent (D) may have any of the following configurations: 1) the layer containing the enzyme (A), the layer containing the enzyme (B), and the layer containing the enzyme (F) are laminated or arranged in parallel on a base member; 2) the layer containing the enzyme (B), the layer containing the enzyme (A), and the layer containing the enzyme (F) are laminated or arranged in parallel on a base member; and 3) the layer containing the enzyme (A) and the enzyme (B) and the layer containing the enzyme (F) are laminated or arranged in parallel on a base member. In each of the above configurations, the layers are disposed in the indicated order from the side that comes into contact with the analyte.

The present disclosure relates to the following aspects.

[1] A method for measuring an analyte using an enzyme (A) that acts on the analyte to produce a product (C) and an enzyme (B) that specifically detects the product (C), the method including the steps of:

i) preparing a reagent (D) in which the enzyme (A) and the enzyme (B) coexist in the absence of the analyte;

ii) bringing the analyte into contact with the enzyme (A) and the enzyme (B) so that the enzyme (A) acts on the analyte to produce a product (E), on which the enzyme (B) does not substantially act, from the analyte;

iii) producing a product (C) by allowing the enzyme (A) or an enzyme (F) that is different from the enzyme (A) that acts on the analyte to produce a product (C) to act on the analyte and/or the product (E); and iv) detecting the product (C) by the enzyme (B).

[2] A method for measuring an analyte using an enzyme (A) that acts on the analyte and an enzyme (B) that specifically detects a product (C) produced from the analyte, the method including the steps of:

i) preparing a reagent (D) in which the enzyme (A) and the enzyme (B) coexist in the absence of the analyte;

ii) bringing the analyte into contact with the reagent (D) so that the enzyme (A) acts on the analyte to produce a product (E), on which the enzyme (B) does not substantially act, from the analyte;

iii) producing a product (C) by allowing the enzyme (A) or an enzyme (F) that is different from the enzyme (A) to act on the analyte and/or the product (E); and iv) detecting the product (C) by the enzyme (B).

[3] The method according to [1] or [2], wherein the reagent (D) is a commercially available package that includes the enzyme (A), the enzyme (B), and a container in which the enzyme (A) and the enzyme (B) are packaged, or a reagent in part of the commercially available package.

[4] The method according to any one of [1] to [3], wherein the step iii) is performed by further adding the enzyme (A) after the step ii).

[5] The method according to any one of [1] to [3], wherein the step iii) is performed by adding the enzyme (F) after the step ii).

[6] The method according to any one of [1] to [3], wherein the step iii) is performed by activating the enzyme (A) after the step ii).

[7] A method for measuring an analyte using an enzyme (A) that acts on the analyte and an enzyme (B) that specifically detects a product (C) produced from the analyte, the method including the steps of:

ii') bringing the analyte into contact with a dry reagent (D) containing the enzyme (A) and the enzyme (B) so that the enzyme (A) acts on the analyte to produce a product (E), on which the enzyme (B) does not substantially act, from the analyte;

iii') producing a product (C) by allowing the enzyme (A) to act on the analyte and/or the product (E); and iv) detecting the product (C) by the enzyme (B).

[8] The method according to [7], wherein the dry reagent (D) includes a first reagent layer that includes a reagent layer containing the enzyme (A) and a reagent layer containing the enzyme (B).

[9] The method according to [7] or [8], wherein the dry reagent (D) further includes a second reagent layer containing an enzyme (F), and in the step iii'), the product (C) is produced by allowing the enzyme (A) and the enzyme (F) to act on the analyte and/or the product (E).

[10] The method according to any one of [1] to [9], wherein the analyte is a glycated protein.

[11] The method according to [10], wherein the glycated protein is selected from the group consisting of glycated hemoglobin, glycated albumin, HbA1c, and a combination thereof.

[12] The method according to any one of [1] to [6], [9], and [10], wherein the enzyme (A) and the enzyme (F) are proteases.

[13] The method according to any one of [1] to [12], wherein the enzyme (B) is a fructosyl amino acid oxidase (FAOD).

[14] The method according to any one of [1] to [13], wherein the product (E) is a glycated peptide that includes a glycated amino acid and has not less than 7 amino acid residues.

[15] A commercially available package used for the method according to any one of [1] to [14], including the enzyme (A), the enzyme (B), and a container in which the enzyme (A) and the enzyme (B) are packaged.

[16] A reagent kit used for the method according to any one of [1] to [6] and [10] to [14], including a reagent container in which the enzyme (A) and the enzyme (B) coexist.

[17] The reagent kit according to [16], further including the enzyme (A) or the enzyme (F) that is packaged in a different container.

[18] A reagent kit for measuring a glycated protein including a reagent container in which a protease and a fructosyl amino acid oxidase (FAOD) coexist.

[19] A method for measuring a content of glycated protein by treating a glycated protein in a serum or plasma sample with a protease to produce a glycated amino acid and/or a glycated peptide and treating the glycated amino acid and/or the glycated peptide with a fructosyl amino acid oxidase,
the method including:
bringing the glycated protein in the sample into contact with the protease and the fructosyl amino acid oxidase simultaneously and then adding a protease that is different from the protease, so that the glycated protein is hydrolyzed to produce a glycated amino acid and/or a glycated peptide; and
reacting the glycated amino acid and/or the glycated peptide thus produced with the fructosyl amino acid oxidase and a color-developing reagent in the presence of a peroxidase.

[20] A method for measuring a content of glycated protein by treating a glycated protein in a serum or plasma sample with a protease to produce a glycated amino acid and/or a glycated peptide and treating the glycated amino acid and/or the glycated peptide with a fructosyl amino acid oxidase,
the method including:
bringing the sample into contact with a dry reagent containing the protease and the fructosyl amino acid oxidase and then adding a protease that is different from the protease, so that the glycated protein in the sample is hydrolyzed to produce a glycated amino acid and/or a glycated peptide; and
reacting the glycated amino acid and/or the glycated peptide thus produced with the fructosyl amino acid oxidase and a peroxidase.

Hereinafter, the present invention will be described in detail by way of examples. However, the present invention is not limited to the following examples.

EXAMPLES

The present specification uses the following abbreviations.
TES: N-Tris(hydroxymethyl)methyl-2-aminoethanesulfonic acid
EDTA: ethylenediaminetetraacetic acid
POD: peroxidase
HTIB: [Hydroxy(tosyloxy)iodo]benzene
TAPS: N-[Tris(hydroxymethyl)methyl]-3-aminopropanesulfonic acid sodium
4-AA: 4-Aminoantipyrine The proteases used were thermolysin (manufactured by Wako Pure Chemical Industries, Ltd., derived from *Bacillus thermoproteolyticus*) and Savinase® (manufactured by Novozymes, derived from *Bacillus clausii*). The FAOD used was FAOD-E (product name, manufactured by Kikkoman Corporation, derived from recombinant *E. coli*).

Example 1

Glycated albumin was measured by preparing the following first reagent (reagent (D)) and second reagent, and using a standard solution (product name: Lucica GA-L, calibrator, manufactured by Asahi Kasei Pharma Corp.) as a sample.

| (First reagent: reagent (D)) | |
|---|---|
| TES | 50 mmol/L |
| Mg-EDTA | 3 mmol/L |
| $CaCl_2$ | 5 mmol/L |
| Triton X-100 | 0.3% |
| POD | 25 KU/L |
| HTIB | 4 mmol/L |
| FAOD (enzyme (B)) | 80 KU/L |
| Thermolysin (enzyme (A)) | 4000 KU/L |
| pH 8.2 | |
| (Second reagent) | |
| TAPS | 180 mmol/L |
| 4-AA | 5 mmol/L |
| POD | 80 KU/L |
| Savinase ® (enzyme (F)) | 8000 KU/L |
| pH 8.0 | |

2 µL of the sample and 8 µL of a specimen diluent were mixed, to which 80 µL of the first reagent (reagent (D)) was added, and then a measurement was started. 20 µL of the second reagent was added 5 minutes after the start of the measurement. The specimen diluent was purified water. The measurement was performed using an automatic analyzer (BM-1650 manufactured by JEOL Ltd.) at measurement wavelengths of 546 nm (main wavelength) and 694 nm (sub-wavelength). A blank absorbance was measured in the same manner except that a physiological saline solution was used as the sample. The measured value was determined by subtracting the blank absorbance from the absorbance obtained by using the standard solution as the sample. FIG. 1 shows the results.

Comparative Example 1

As Comparative Example 1, a measurement was performed in the same manner as Example 1 except that the following first reagent-2 was used instead of the first reagent. FIG. 1 shows the results.

(First Reagent-2)

| TES | 50 mmol/L |
|---|---|
| Mg-EDTA | 3 mmol/L |
| $CaCl_2$ | 5 mmol/L |
| Triton X-100 | 0.3% |
| POD | 25 KU/L |
| HTIB | 4 mmol/L |
| FAOD (enzyme (B)) | 80 KU/L |
| pH 8.2 | |

As shown in FIG. 1, since the first reagent (reagent (D)) in which the protease and the FAOD coexisted was used in Example 1, the reaction ended quickly, and the absorbance 10 minutes after the start of the measurement was increased compared to Comparative Example 1, in which the FAOD was added as the first reagent, and then the protease was added as the second reagent. Therefore, it was confirmed that the product (C) was produced from the analyte efficiently in a shorter time with the use of the first reagent (reagent (D)) in which the protease and the FAOD coexisted, and thus the measurement accuracy of the analyte was improved.

As Example 1-1, measurements were also performed in the same manner as Example 1 except that each of the following enzymes was added as the enzyme (A) instead of thermolysin. Moreover, as Comparative Example 1-1, a measurement was performed in the same manner as Example 1 except that the enzyme (A) was not added to the first reagent.

| | |
|---|---|
| Trypsin (from porcine pancreas) | 500 KUSPUnit/L |
| Trypsin (from bovine pancreas) | 18 KU/L |
| α-chymotrypsin (from bovine pancreas) | 10 KU/L |
| Alcalase ™ | 13 AU-A/L |
| Neutral protease | 1300 KU/L |

The absorbance was determined by subtracting "the absorbance immediately before the addition of the second reagent" from "the absorbance 5 minutes after the addition of the second reagent". The resultant absorbance was 59 mAbs. for trypsin (from porcine pancreas), 58 mAbs. for trypsin (from bovine pancreas), 54 mAbs. for α-chymotrypsin (from bovine pancreas), 54 mAbs. for Alcalase, and 55 mAbs. for neutral protease, as compared to 52 mAbs. in Comparative Example 1-1 (in which the enzyme (A) was not added to the first reagent).

The fact that the absorbance 5 minutes after the addition of the second reagent was higher in Example 1-1 than in Comparative Example 1-1 indicates that the product (C) was produced from the analyte more efficiently in a larger amount with the use of the first reagent (reagent (D)) in which the protease and the FAOD coexisted. Thus, it was confirmed that the measurement accuracy of the analyte was improved.

Example 2

Figure 2:
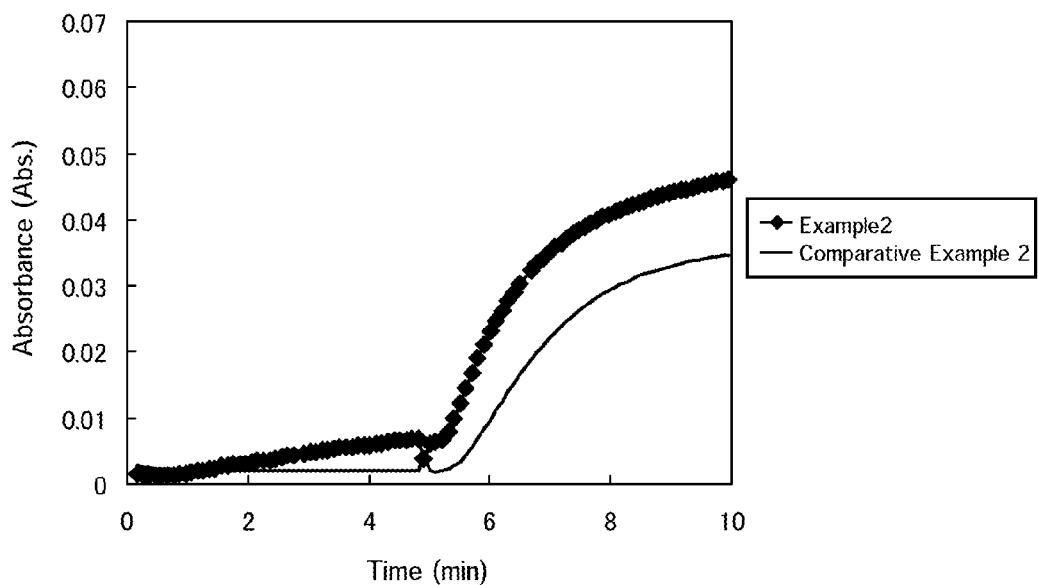
FIG. 2 is a graph showing the results of Example 2 and Comparative Example 2.

A measurement was performed in the same manner as Example 1 except that a normal human serum was used as a sample. FIG. 2 shows the results.

Comparative Example 2

As Comparative Example 2, a measurement was performed in the same manner as Comparative Example 1 except that a normal human serum was used as a sample. FIG. 2 shows the results.

As shown in FIG. 2, since the first reagent (reagent (D)) in which the protease and the FAOD coexisted was used in Example 2, the reaction ended quickly, and the absorbance 10 minutes after the start of the measurement was increased compared to Comparative Example 2, in which the FAOD was added as the first reagent, and then the protease was added as the second reagent.

Example 3

A reagent was prepared by adding thermolysin (protease) to the first reagent of a commercially available reagent for measuring glycoalbumin (product name: Lucica GA-L, glycoalbumin reagent, manufactured by Asahi Kasei Pharma Corp.). Glycated albumin was measured by using this reagent as the reagent (D) and the standard solution (product name: Lucica GA-L, calibrator, manufactured by Asahi Kasei Pharma Corp.) as a sample.

Figure 3:
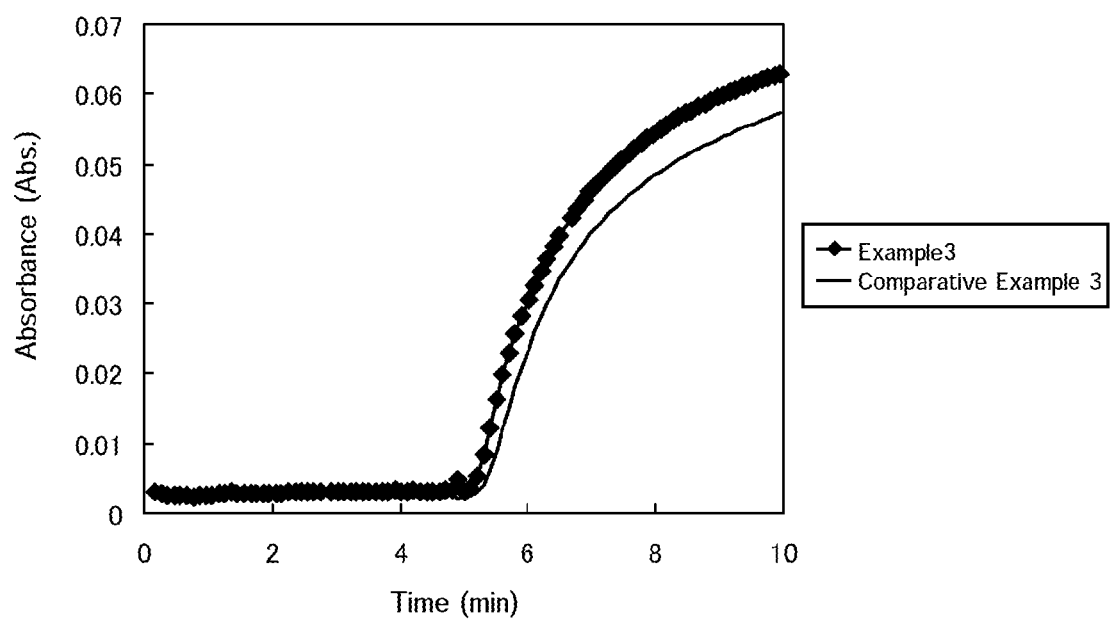
FIG. 3 is a graph showing the results of Example 3 and Comparative Example 3.

Specifically, 4000 KU/L of thermolysin (enzyme (A)) and 5 mmol/L of $CaCl_2$ were added to the first reagent of the glycoalbumin reagent in Lucica GA-L, thereby providing a reagent in which KAOD (ketoamine oxidase, enzyme (B)) and thermolysin (enzyme (A)) coexisted. A measurement was performed in the same manner as Example 1 except that the above reagent was used instead of the first reagent of Example 1, and the second reagent of the glycoalbumin reagent in Lucica GA-L was used as the second reagent of Example 1. FIG. 3 shows the results.

Comparative Example 3

As Comparative Example 3, a measurement was performed in the same manner as Example 3 except that the first reagent of the glycoalbumin reagent in Lucica GA-L was used as it was. FIG. 3 shows the results.

As shown in FIG. 3, since the first reagent (reagent (D)) in which the protease and the KAOD coexisted was used in Example 3, the reaction ended quickly, and the absorbance 10 minutes after the start of the measurement was increased compared to Comparative Example 3, in which the KAOD was added as the first reagent, and then the protease was added as the second reagent.

The present invention is useful in the fields of medicine, life science, and biological research.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. A method for measuring a glycated protein using a protease enzyme (A) that acts on the glycated protein and fructosyl amino acid oxidase (FAOD) enzyme (B) that specifically detects a glycated amino acid product (C) produced from the glycated protein, the method comprising steps of:
   i) preparing a reagent (D) in which the protease enzyme (A) and the fructosyl amino acid oxidase (FAOD) enzyme (B) coexist in the absence of the glycated protein;
   ii) bringing the glycated protein into contact with the reagent (D) to form a reaction mixture so that the protease enzyme (A) acts on the glycated protein to produce a glycated peptide product (E), on which fructosyl amino acid oxidase (FAOD) enzyme (B) does not substantially act;
   iii) producing a glycated amino acid product (C) by adding to the reaction mixture a protease enzyme (F) that is different from the protease enzyme (A) to act on the glycated peptide product (E); and
   iv) detecting the glycated amino acid product (C) in the reaction mixture with the fructosyl amino acid oxidase (FAOD) enzyme (B), peroxidase (POD) and a color-developing reagent to produce a detectable color.

2. The method according to claim 1, wherein the reagent (D) is a commercially available package that includes the enzyme (A), the enzyme (B), and a container in which the enzyme (A) and the enzyme (B) are packaged, or a reagent in part of the commercially available package.

3. The method according to claim 1, wherein the step iii) is performed by adding the enzyme (F) after the step ii).

4. The method according to claim 1, wherein the glycated protein is selected from the group consisting of: glycated hemoglobin (HbA1c), glycated albumin, or a combination thereof.

5. The method according to claim 1, wherein protease enzyme (A) enzyme (A) has a narrow substrate specificity.

6. The method according to claim 1, wherein protease enzyme (A) is selected from the group consisting of: thermolysin, trypsin, α-chymotrypsin, Alcalase, a neutral protease, and an alkaline protease.

7. The method according to claim 1, wherein the reagent (D) is in dry form.

8. The method according to claim 7, wherein the dry reagent (D) includes a first reagent layer that includes a reagent layer containing the enzyme (A) and a reagent layer containing the enzyme (B).

9. The method according to claim 7, wherein the dry reagent (D) further includes a second reagent layer containing an enzyme (F), and in the step iii), the product (C) is produced by allowing the enzyme (A) and the enzyme (F) to act on the analyte and/or the product (E).

\* \* \* \* \*